(12) United States Patent
Brasset et al.

(10) Patent No.: US 10,004,922 B2
(45) Date of Patent: Jun. 26, 2018

(54) APPARATUS FOR GENERATING FOCUSED ULTRASOUND WAVES WITH REDUCED TREATMENT TIME

(71) Applicants: EDAP TMS FRANCE, Vaulx-en-Velin (FR); INSTITUT NATIONAL DE LA SANTE ET DE LA RECHERCHE MEDICALE—I.N.S.E.R.M., Paris (FR)

(72) Inventors: Lucie Brasset, Villeurbanne (FR); Jean-Yves Chapelon, Villeurbanne (FR); Nicolas Guillen, Fontaine sur Saone (FR); Francoise Chavrier, Chezeneuve (FR); Emmanuel Blanc, Saint-Didier au Mont D'Or (FR)

(73) Assignees: EDAP TMS FRANCE, Vaulx-en-Velin (FR); INSTITUT NATIONAL DE LA SANTE ET DE LA RECHERCHE MEDICALE-I.N.S.E.R.M., Paris (FR)

( * ) Notice: Subject to any disclaimer, the term of this patent is extended or adjusted under 35 U.S.C. 154(b) by 0 days. days.

(21) Appl. No.: 14/522,008

(22) Filed: Oct. 23, 2014

(65) Prior Publication Data
US 2015/0112235 A1    Apr. 23, 2015

(30) Foreign Application Priority Data
Oct. 23, 2013   (FR) .................... 13 60343

(51) Int. Cl.
*A61B 1/00*     (2006.01)
*A61N 7/02*     (2006.01)
*A61N 7/00*     (2006.01)

(52) U.S. Cl.
CPC ........ *A61N 7/02* (2013.01); *A61N 2007/0078* (2013.01); *A61N 2007/0091* (2013.01); *A61N 2007/0095* (2013.01)

(58) Field of Classification Search
CPC .................................. A61N 7/02; A61N 7/00
See application file for complete search history.

(56) References Cited

U.S. PATENT DOCUMENTS 5,665,054 A    9/1997 Dory
6,488,639 B1   12/2002 Ribault et al.
(Continued)

FOREIGN PATENT DOCUMENTS

| DE | 69417639 T2 | 9/1999 |
|---|---|---|
| WO | 2009050719 A2 | 4/2009 |
| WO | 20100127369 A1 | 11/2010 |

OTHER PUBLICATIONS

French Search Report dated Jul. 2014, corresponding to French Patent Application 1360343.
(Continued)

*Primary Examiner* — Hien Nguyen
(74) *Attorney, Agent, or Firm* — Ladas & Parry LLP

(57) ABSTRACT

The object of the invention relates to an apparatus for the thermal treatment of biological tissues by means of the application of focused ultrasound waves, the apparatus including: a probe movement system for ensuring: the moving of the focal zone along a first direction, from a distal point of the treatment zone to a proximal point of the treatment zone, in order to create a sequence of elementary treatment zones; the juxtaposition of sequences of elementary treatment zones in order to completely cover the treatment zone; a control circuit controlling the probe, in order to ensure that the ultrasonic power delivered to the focal zone decreases between the distal point and the proximal point of the treatment zone.

8 Claims, 2 Drawing Sheets

(56) References Cited

U.S. PATENT DOCUMENTS

2011/0144544 A1  6/2011  Fan et al.
2013/0041249 A1  2/2013  Salomir et al.
2013/0261461 A1  10/2013 Murakami

OTHER PUBLICATIONS

Joshua Coon et al:"HIFU treatment time reduction in superficial tumours through focal zone path selection", International Journal of Hyperthermia, Basingstoke, GB, vol. 27, No. 5, Aug. 1, 2011, pp. 465-481.

APPARATUS FOR GENERATING FOCUSED ULTRASOUND WAVES WITH REDUCED TREATMENT TIME

This application claims priority to French Application No. 1360343, filed Oct. 23, 2013.

The present invention relates to the technical field of devices or apparatuses having an ultrasound probe capable of emitting in a focal zone, high intensity focused ultrasound (HIFU).

The object of the invention finds particularly advantageous applications in the field of therapeutic treatment by means of focused ultrasonic waves.

In a conventional sense, the principle underlying therapeutic ultrasound consists of focusing an ultrasonic beam emitted by an ultrasound probe, on a target zone of the biological tissue in the human body, for example. The ultrasound propagates from the probe to the focal point while passing through the biological tissues, with a part of their energy being absorbed by these tissues and converted into heat. The rise in temperature takes place preferably in the ultrasound focusing zone (focal volume), where the amplitude and the intensity of the ultrasonic waves are at the maximum. When the rise in temperature and the time during which the tissues are subjected to this temperature exceed a certain threshold (thermal dose), an irreversible destruction of tissues is brought about. The tissues situated between the focusing zone and the ultrasound probe are subjected to far less intense heating and the natural vascular system provides the ability to evacuate the thermal input in a manner such that these tissues do not suffer any damage.

This technique is interesting insofar as it provides the ability to destroy biological tissues by way of extracorporeal or endocardial mode, that is to say without necessitating surgical incision. The principle of focused ultrasound therapy is applied, for example, to the treatment of malignant tumours of the prostate, kidney or liver, but also to the treatment of benign tumours, such as uterine fibroids, for example. The U.S. Pat. No. 1,858,591 describes this therapeutic technique in the context of the treatment of prostate cancer.

The duration of treatment therapies is recognised as being a highly limiting factor with respect to applications of focused ultrasound therapies. Thus, these treatments are geared mainly towards small organs, or small tumours in organs. The duration of treatments has resulted essentially from two effects:

the effect of focusing which causes the ultrasonic beam to converge in a volume that typically amounts to a few cubic millimeters ($mm^3$) only. In order to cover the entire given organ or a tumour in its entirety, it is therefore necessary to repeat the ultrasonic pulses and juxtapose them. Hundreds of pulses are thus required. Each of these can take several seconds and the treatment itself can last an hour or more depending on the volume of treatment;

the repeating of ultrasonic pulses brings about accumulated heat deposition in the tissues located between the ultrasound probe and the focusing zone. In order to allow sufficient time for the natural vascular system to dissipate this accumulated heat buildup, it is necessary to provide for a waiting time between subsequent pulses, during which time period the emission gets interrupted. This waiting time happens to further lengthen the duration of treatment. The ratio of the time of emission of the ultrasonic pulse to the period of repetition of the ultrasonic pulses defines the duty cycle associated with the emission sequence. Typically the duty cycle ratios obtained are in the order of 50%, that is to say that the time period of emission of the ultrasonic pulse is of the order of the waiting time period.

Thus, in order to reduce the treatment time, a first category of solutions consists of increasing the volume of the necrotic zone by increasing the volume of the focal zone and thereby reducing the number of ultrasonic pulses required to cover the treatment volume.

In order to increase the volume of the necrotic zone, the power of the ultrasonic pulse may be increased or the ultrasonic pulse may be maintained beyond the time necessary for the formation of the lesion in the focal volume. The biological lesion will then extend beyond the focal volume in particular along the direction of the probe. The dynamics of the formation of the tissue lesion make it possible to modulate the extension of the necrotic zone, but it has the effect of over-treating the focal zone. Furthermore, the maintenance of the ultrasonic pulse for long durations would require, in order to preserve the intermediate tissue, increasing the wait time between subsequent pulses, that is to say to reducing the duty cycle ratio, which is contrary to the initial goal of reducing the treatment time.

The document EP 1 274 483 proposes to increase the volume of the focal zone by increasing the aperture number of the probe, that is to say the ratio of the focal length to the diameter of the emitting surface. The diameter of the emitting surface is reduced by suppressing the emission of groups of independent concentric rings. However, the reduction of the aperture of the probe has the effect of increasing the acoustic intensity on the tissues located between the focal zone and the probe. In order to avoid damaging them, it then becomes necessary to reduce the acoustic energy delivered or to increase the waiting time between subsequent pulses.

The technique called "split focus" is also known to increase the volume of the focal zone. It consists of dividing the emission surface of the ultrasound probe into several sectors supplied with power in phase opposition with a view to creating as many focal points as there are individual sectors. The acoustic intensity in the focal volume is thus reduced and it is necessary to increase the acoustic energy delivered by the probe in order to maintain the same therapeutic effect at the risk of damaging intermediate tissue.

The document EP 2 035 091 proposes the increasing of the focal volume by fabricating the ultrasound probe according to a toroidal geometry. Using this geometry for the probe makes it possible to form a double focal zone and to consequently increase the volume of treatment in a consistent manner. This solution lends itself well to the rapid treatment of isolated large volume tumours in an organ and does not necessitate the preservation of the surrounding tissues, but is less well suited to the treating of small volume tumours with precision.

The patent application US 2011/144544 describes a mechanical device for moving the focal point of the transducer so as to scan a large volume of tissue in a minimal amount of time.

A second category of solutions consists of reducing the waiting time between subsequent ultrasonic pulses. Thus, the document FR 2 903 315 provides for eliminating the waiting time between subsequent ultrasonic pulses by segmenting the emission surface into at least two parts that are supplied with power independently, alternatively, and substantially consecutively. This technique enables the continuous heating of the focal zone and also the increasing of the focal volume by reducing the aperture of the probe. But it is also necessary to reduce the acoustic energy transmitted by each of the segments of the probe in order to avoid damaging the intermediate tissues. Consequently, the same energy is delivered to the tissues in a continuous manner without reducing the treatment time.

The patent application WO 2010/127369 also provides, in the area of treatment by sonoporation, for modulating the duty cycle by considering continuous emission.

The patent U.S. Pat. No. 5,665,054 describes a method based on rapid movement of the focal point of an ultrasonic transducer in the focal plane in order to obtain a constant temperature distribution in a large volume. The ultrasonic intensity required to maintain this temperature is not constant in the focal plane, but must be greater in the periphery of the focal volume in order to take into account the effects of heat diffusion.

The patent U.S. Pat. No. 5,665,054 provides for controlling of the energy delivered to the tissues by means of modulating the time period of emission.

In the field of treatment of myocardial tissue using an ultrasound transducer, the patent application US 2013/0261461 discloses an apparatus for moving the focal zone in order to treat the thickness of the muscle. This device controls and commands the stopping of the period of emission of the ultrasonic waves when a hyperechoic zone appears on a monitor. This device provides the ability to control the energy delivered to the tissues by means of modulating the time period of emission.

With a view to reducing the treatment time of focused ultrasound therapies, the published paper "HIFU treatment time reduction in superficial tumours through focal zone path selection" Int. J. Hyperthermia, August 2011; 27 (5): 465-481, offers a study on optimising the scan path trajectories of focal zones.

Various different types of scan path trajectories have been studied including axial trajectories as in axial stacking of lesions and then lateral movement of focal zone, planar trajectories corresponding to a sequential lateral movement and creation of successive treatment planes, circular trajectories for each of the planes or 3D trajectories.

The optimisation of trajectories is achieved by acting both on the emission time and turn off time of the ultrasound probe but not on the ultrasound emission power, which is kept constant for each lesion. Thus, the methodology provided for the application of a time period of emission until the thermal dose level has been reached, and a turn off time lasting for an optimised period allowing for the cooling of the interface tissues. The thermal dose level previously deposited by preceding shots is subtracted from that to be reached. In contrast, the thermal dose resulting from subsequent shots is not taken into account. In total, there appears to be too high a dose.

It becomes apparent from the study that the treatments based on trajectories from stacking of lesions along the acoustic axis are more rapid than those based on lateral movements. Similarly, it is also clear from this study that the treatment is faster when starting with the intermediate plane, as compared to a treatment commencing with the distal plane. Furthermore, this study recommends increasing the power emitted by the ultrasound probe in order to reduce the treatment time.

The simulations carried out in this study relate to treatment of volumes of small size, measuring less than 5 $cm^3$. For volumes measuring 5 $cm^3$, the study shows that it is necessary for the turn off time of the ultrasonic emission to be increased until it reaches 90% of the treatment time, which is a duty cycle of 10%, so as to allow for cooling of the interface tissues. The transposition to even larger volumes, typically measuring from 30 $cm^3$ to 40 $cm^3$, requires treatment times that are increased in proportion, which are incompatible with clinical use.

The patent application US 2013/041249 describes a method for regulating the thermal dose by means of modulating the energy delivered to the tissues. This modulation is obtained by modulating the emission time period and then if this modulation is insufficient, by subsequently adjusting the power. It should be noted that the reduction in the duration of shots and maintenance of high power levels are instead chosen in order to obtain a greater biological effect and a better controlled extension. This document does not provide a solution with reduction of the treatment time.

The object of the invention is aimed at overcoming the drawbacks of earlier known solutions by providing a new treatment apparatus that ensures the application of focused ultrasound waves to a large volume treatment zone, while providing the ability to significantly reduce the time of treatment of the said zone.

In order to achieve such an objective, the apparatus for the thermal treatment of biological tissues acts in a treatment zone, by means of the application of focused ultrasound waves, the apparatus comprising:

an ultrasound probe delivering focused ultrasound energy in a focal zone located at a distance from the probe;

a control system for controlling the ultrasound probe so as to move the focal zone along a predetermined scan path trajectory and for controlling the ultrasonic power delivered, in the form of a repetition of ultrasonic pulses, each being separated by a waiting time and having an emission time whose ratio to the period of repetition of ultrasonic pulses defines the duty cycle. According to the invention, the control system includes:

a probe movement system for ensuring:
the moving of the focal zone along a first direction, from a distal point of the treatment zone to a proximal point of the treatment zone, in order to juxtapose the elementary treatment zones and to create a sequence of elementary treatment zones;
the juxtaposition of sequences of elementary treatment zones along at least one second direction that is different from the first direction, in order to completely cover the treatment zone;

a control circuit controlling the probe, in order to ensure that the ultrasonic power delivered to the focal zone decreases between the distal point and the proximal point of the treatment zone.

The apparatus according to the invention also includes a combination of one and/or another of the following additional characteristic features:

the control circuit controls the probe such that the duty cycle ratio of the ultrasonic pulses used for creating the sequences of elementary zones is comprised between 65% and 100% and preferably between 85% and 100%;

the control system brings about the movement of the focal zone along the acoustic axis that serves as a first direction;

the control system includes a mechanical system for moving the ultrasound probe in order to ensure the movement of the focal zone;

the ultrasound probe comprises a plurality of ultrasound emitters and in that the control system includes a system which electronically controls the ultrasound emitters in order to ensure the movement of the focal zone;

the control system controls the ultrasound emitters in a manner such that the "aperture number" or "F number" of the transducer, that is to say the ratio of the focal length to the diameter of the probe formed by the activated ultrasound emitters, decreases when the focal zone passes from the distal point to the proximal point;

the control system ensures the reduction of the ultrasonic power emitted in accordance with a correction law $p_i$ such as for example:

$$p_i = P_{ref} \exp(Ad_i)$$

Where:

$p_i$=power required (Watts) for a focal zone at the depth $d_i$ (cm).

$P_{ref}$=reference power (Watts)

A=attenuation coefficient ($cm^{-1}$).

Various other characteristic features become apparent from the description provided here below with reference made to the accompanying drawings which show, by way of non limiting examples, implementation forms or embodiments of the object of the invention.

Figure 1:
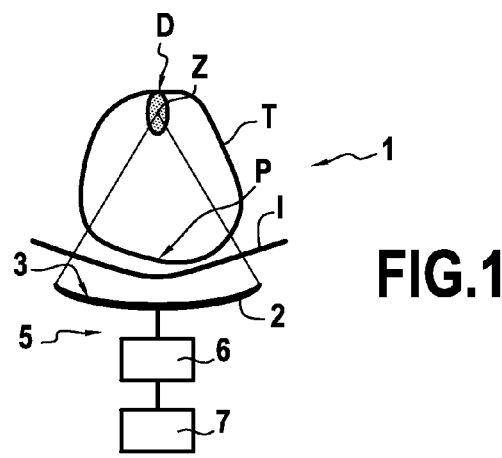
FIG. 1 is a diagrammatic view of an apparatus to be used for the thermal treatment in accordance with the invention.

As may be seen more clearly in FIG. 1, the object of the invention relates to an apparatus 1 for the thermal treatment of biological tissues in a zone of treatment T, by means of the application of High Intensity Focused Ultrasound (HIFU). This treatment apparatus conventionally comprises an ultrasound probe 2, which is presented in the form of a transducer, having an emission surface 3 for emitting focused ultrasound waves in a focal zone Z corresponding to an elementary zone of treatment. The geometry of this focal zone Z depends on the shape of the emission surface. Typically, the transducer includes one or more ultrasound emitters such as, for example piezoelectric elements.

In a known manner, this ultrasound probe 2 is positioned by way of extracorporeal or endocardial mode, in the proximity of the zone of interface I of the biological tissues with at least one part thereof to be treated. To the extent that the tissues to be treated (that is to say the zone of treatment T) occupy a volume that is greater than the elementary zone of treatment (corresponding to the focal zone, Z), the focal zone Z of the ultrasound probe 2 must then be moved along a predetermined scan path trajectory in order to completely treat the tissues in the treatment zone T.

The apparatus 1 also includes a control system 5 for controlling the ultrasound probe 2 in order to move the focal zone Z along a predetermined trajectory and for controlling the ultrasonic energy delivered by the ultrasound probe. Such a control system 5 includes in particular a control circuit 6 that outputs signals for activating the ultrasound emitters via a stage of amplification, and a system 7 for moving the focal zone Z along a predetermined trajectory. Such a control circuit 6 is not described in more precise detail since the development thereof falls within the scope of common technical knowledge of the person skilled in the art. In addition, as will be described in the remaining sections of the description, the system 7 for moving the focal zone Z is "mechanical" and/or "electronic" in nature.

In accordance with the invention, the probe movement system 7 ensures:

the moving of the focal zone Z along a first direction X from a distal point D of the treatment zone T to a proximal point P of the treatment zone T in order to juxtapose the elementary treatment zones and to create a sequence S of elementary treatment zones;

the juxtaposition of the sequences S1, S2, S3, . . . , of elementary treatment zones along at least one second direction Y that is different from the first direction X, in order to completely cover the treatment zone T.

The control system 5 controls the probe 2 by making use of the control circuit 6 in order to ensure that the ultrasonic power delivered to the focal zone Z decreases between the distal point D and the proximal point P of the treatment zone. According to an advantageous variant of the implemented embodiment, the control circuit 6 is controlled in a manner such that the duty cycle ratio of the ultrasonic pulses used for creating the sequences of elementary zones is comprised between 65% and 100% and preferably between 85% and 100%. It is recalled that the control circuit 6 controls the ultrasound probe in a manner such that the ultrasonic power delivered is in the form of ultrasonic pulses (or shots) each separated from the other by a waiting time. The ratio of the emission time over the period of repetition of the ultrasonic pulses defines the duty cycle.

In the example of embodiment illustrated in the FIGS. 1A to 1F, the control system 5 includes, by way of a probe movement system 7, a mechanical device for moving the ultrasound probe 2 in order to ensure the movement of the focal zone Z so as to cover the entire treatment zone T based on the sequences of elementary zones and the juxtapositions thereof. In other words, the ultrasound probe 2 is moved in the space by any known mechanical system so as to follow the scan path trajectory described here above.

Figure 1A:
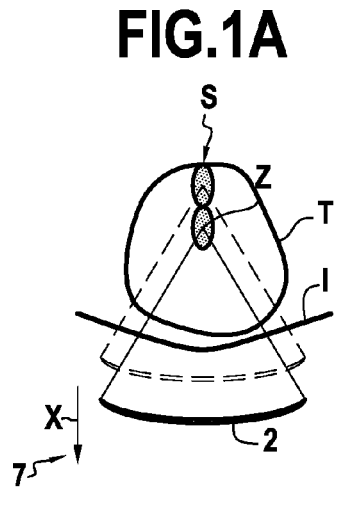
FIGS. 1A to 1F are different views of implementation of a first variant embodiment of a treatment apparatus in accordance with the invention.

According to the example of embodiment illustrated in the FIGS. 1A to 1E, the control system 5, and more precisely the probe movement system 7, ensures the movement of the focal zone Z along a first direction X which, preferably, is coincident with the acoustic axis of the ultrasound probe. The control system 5 thus positions the focal zone Z in its position which is the deepest or farthest away from the ultrasound probe 2. In this position, illustrated in the FIG. 1, the control system 5 and more precisely the control circuit 6 is controlled so as to create the elementary lesion at a power $P_i$, with a duration of the ultrasonic pulse being equal, for example, to one second. Then, by making use of the probe movement system 7, the ultrasound probe 2 is physically retracted in order to position the focal zone Z in a second position resulting in a second elementary lesion juxtaposed with the preceding lesion (FIG. 1A). The juxtaposition of the second lesion relative to the first should allow for homogenous or uniform treatment of the treatment zone T, that is to say, without over-treatment or under-treatment. In order to bring this about the lesions may be juxtaposed with or without overlapping relative to one another. In this second position of the focal zone Z, the ultrasound probe 2 emits an ultrasonic pulse within a minimal period of time from the creation of the first focal zone.

Given that the second elementary lesion is to be created at a lesser depth, the power of the ultrasonic pulse is reduced in order to maintain the same volume of elementary lesion. The law for correction of the power is of the type $p_i$ such as for example:

$$p_i = P_{ref} \exp(Ad_i)$$

Where:
$p_i$=power required (Watts) for a focal zone at the depth $d_i$ (cm).
$P_{ref}$=reference power (Watts)
A=attenuation coefficient ($cm^{-1}$).

The attenuation coefficient A is characteristic of the tissue treated, the frequency of the ultrasonic waves and the conditions of treatment. For example, a tissue that has been previously heated or in which cavitation bubbles are formed will present an attenuation coefficient that is different from the initial one.

The law for correction of the power provided by way of an example is particularly suitable for the treatment of large volumes located at a significant distance from the interfaces and necessitating the juxtaposing of several elementary focal zones. For shallower lesions, the power correction law may take the simpler form of a linear function. The essential element is that this power correction law induces a decrease in the power between the ultrasonic pulses generated in the distal zone and those generated in the proximal zone.

Figure 1B:
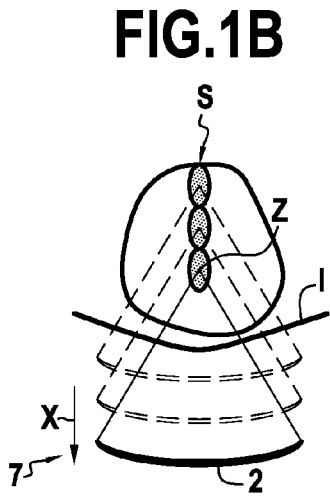
Figure 1C:
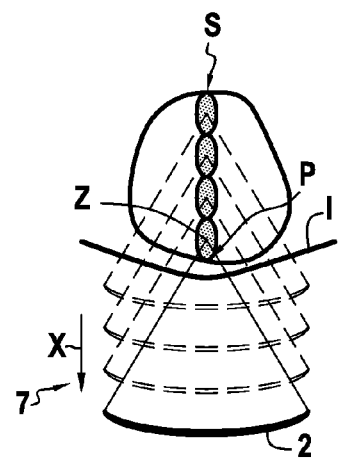

As it becomes more clearly apparent from the FIGS. 1B and 1C, the control system 5 repeats the operations of moving the focal zone Z along the first direction X, from the distal point D to the proximal point P, and the operations of emission of the ultrasonic pulses, with on the one hand, a power level that decreases between the distal point D and the proximal point P, and on the other hand, in accordance with an advantageous variant of the implemented embodiment, the duty cycle ratio of the ultrasonic pulses used for creating the sequences of elementary zones that is comprised between 65% and 100% and preferably between 85% and 100%.

The moving of the focal zone Z along the first direction X, from the distal point D to the proximal point P makes it possible to generate a sequence from one to several elementary zones of treatment (four in number in the example shown). Quite obviously, for a given trajectory along the first direction X, the number of elementary lesions may be increased to "infinity" by reducing the interval between each of them so as to tend towards a spatially continuous treatment in which the power may be adjusted in a continuous fashion in accordance with the correction law so as to also tend towards a continuous temporal modulation of the power.

As explained here above, the control system 5 ensures the movement of the focal zone Z from the distal point D to the proximal point P, with an ultrasonic power that decreases between the distal point and the proximal point of the treatment zone. Thus, the acoustic power required for forming each of these elementary lesions is reduced as the elementary lesions get closer to the interface zone I. With the acoustic power levels becoming increasingly weaker, the interface tissues are increasingly less exposed to the heat deposition and the functional effect of the natural vascular system becomes sufficient to dissipate this heat deposition. Therefore, the period of waiting time prior to the launch of the sequence of shots that will provide the ability to juxtapose the subsequent elementary lesion volume can be minimised.

Typically, the apparatus 1 according to the invention provides the ability to create a sequence for example, of 4 elementary treatment zones in 4 seconds. The four ultrasonic pulses each last for one second and follow each other without any wait time period. The duty cycle over this sequence is thus close to 100%. The wait time period varies depending on whether the probe movement system 7 for moving and juxtaposing the focal zones Z and the sequences of elementary treatment zones is "mechanical" and/or "electronic" in nature. If the system 7 is electronic in nature, the waiting time period is negligible compared to the emission time period and the duty cycle ratio approaches 100%. If the system 7 is mechanical in nature, the waiting time period is substantially increased in order to allow for the movement of the probe by using the mechanical means; it may be of the order of 200 ms or even around 500 ms, thus reducing the duty cycle to 85% or even about 65%.

In the prior art documents, a waiting time period of 4 seconds after a pulse from a shot of 4 s, must be adhered to before the subsequent pulse shot so as to allow for the cooling of the interface tissues. The duty cycle ratio is thus 50%. Unlike the previous techniques that impose a waiting time period between the creation of subsequent elementary zones of treatment or a waiting period between the creation of subsequent sequences of elementary zones, the treatment performed with the use of the apparatus 1 according to the invention proceeds with waiting time periods that may be reduced to the minimum possible or even near zero thereby allowing for treatment sequences with duty cycle ratios approaching 100%, or 85% to 65% depending on the probe movement systems. These duty cycle ratios make it possible to reduce the period of treatments to a substantial extent as compared to earlier techniques. In the prior art, for example, the treatment of a treatment zone T requiring the repetition of 500 lesions with a duty cycle ratio of 50% based on 5 seconds of emission and 5 seconds of waiting would last approximately 80 minutes. According to the invention the same treatment conducted with sequences of shots based on a duty cycle of 85% would be conducted within 50 minutes. By way of an example, the volume of the treatment zone T is for example between 25 $cm^3$ and 35 $cm^3$.

Figure 1D:
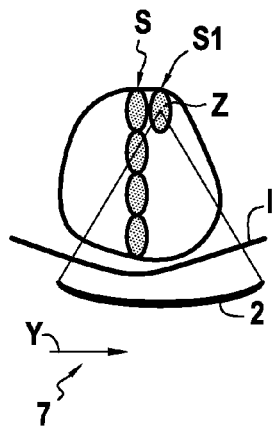
Figure 1E:
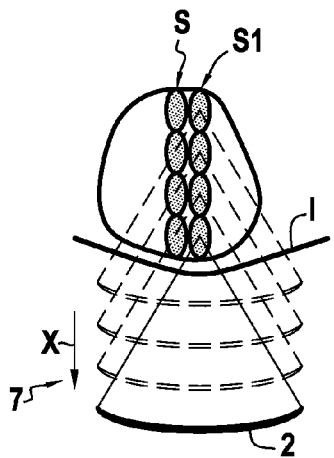
Figure 1F:
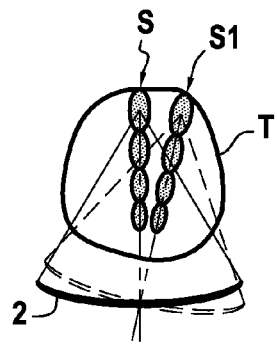

The control system 5 ensures, by means of the probe moving system 7, in the example illustrated in FIGS. 1D and 1E, the movement of the ultrasound probe 2 along the direction Y in order to generate in a juxtaposed manner and within a minimal time period, one or more sequences of elementary treatment zones, S1, S2, S3, . . . , in order to completely cover the treatment zone. The movement of the ultrasound probe 2 along the direction Y may be brought about by translational movement (FIGS. 1D and 1E) or by rotation that allows for sectoral trajectories (FIG. 1F). Quite obviously, the ultrasound probe may be moved along a third direction in order to cover an entire volume.

In accordance with the invention, each of the sequences of elementary treatment zones S1, S2, S3, . . . , is created according to the principle described in relation to FIGS. 1 to 1C. Thus, for each of the sequences of elementary treatment zones S1, S2, S3, . . . , the ultrasonic power delivered in the focal zone Z decreases between the distal point D and the proximal point P of the treatment zone. In addition, according to an advantageous variant of the implemented embodiment, the duty cycle ratio of the ultrasonic pulses used for creating the sequences of elementary treatment zones S1, S2, S3, . . . , is comprised between 65% and 100% and preferably between 85% and 100%. Quite obviously, each of the sequences of elementary treatment zones S1, S2, S3, . . . , includes a number of elementary zones for identical or different treatment. The successive generation of these sequences, with a minimal period of time between them, makes it possible to also limit the treatment time.

It is to be noted that within the context of an endocardial treatment, the physical retraction of the ultrasound probe 2 is often limited by anatomical considerations.

Figure 2:
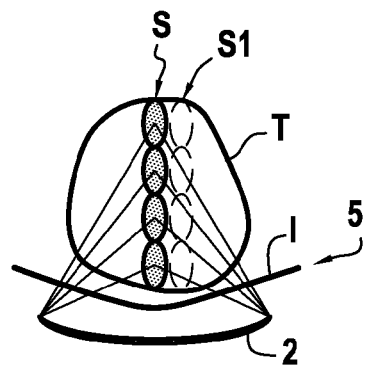
FIG. 2 is a diagrammatic view of another exemplary embodiment of a treatment apparatus in accordance with the invention.

FIG. 2 illustrates another example of embodiment in which the control system 5 includes by way of a probe moving system 7, a system that electronically controls the ultrasound emitters of the probe in order to ensure, by means of a delaying law, the movement along the direction X, of the focal zone Z of the ultrasound probe 2 without mechanical movement.

The moving of the focal zone Z of the ultrasound probe is brought about by electronic means 7 that are known per se. Such a solution consists of having available a probe presenting a plurality of ultrasound emitters distributed for example based on a spherical geometry that makes it possible to divide the emission surface 3 of the ultrasound probe 2, for example into a plurality of independent concentric rings, each being fed by an independent electrical signal making it possible to apply the delaying laws between each of the signals. These delaying laws allow for modifying the position of the point of convergence of the ultrasonic field along the acoustic axis of the ultrasound probe, without physical movement of the ultrasound probe. The power law previously described above is applied with the use of the control circuit 6, when bringing about the juxtaposition of the elementary lesions necessary to obtain a sequence S of elementary treatment zones. In a similar fashion, the passing from the sequence S of elementary treatment zones to the sequence S1 of elementary treatment zones can be done by means of a probe movement system 7 that may be mechanical or electronic in nature. The sequences S1, S2, S3, . . . of elementary treatment zones are juxtaposed within a minimal time period, as explained above.

Figure 2A:
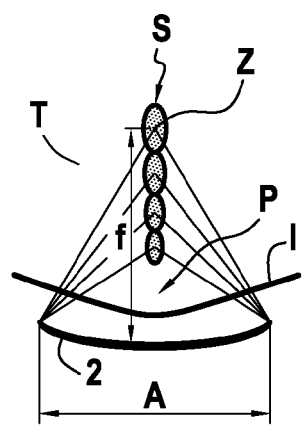
FIGS. 2A and 2B are views illustrating the benefits that may be obtained using a treatment apparatus described in the FIG. 2.

This solution in addition presents the further advantage of providing the ability to create proximity lesions with a geometric configuration of the ultrasound probe for which the aperture number or F number defined as the ratio of the focal length to the diameter of the probe formed by the activated ultrasound emitters, decreases as the elementary lesions are formed in increasing proximity to the ultrasound probe 2. The decrease in the aperture number of the ultrasound probe 2 enables better focusing of the ultrasound field and improved preservation of the intermediate tissues by reducing the ultrasound acoustic intensity over the interface zone I. The optimal focusing of the ultrasonic field also makes it possible to obtain the same acoustic intensity at the focal point with a reduced acoustic power that further allows for the preservation of the intermediate tissues. The optimal focusing also provides the ability to reduce the volume of all of the focal zones Z as the latter get closer to the proximal point P of the treatment zone T as illustrated in FIG. 2A.

Figure 2B:
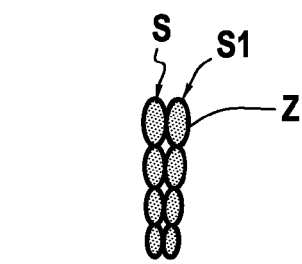

The reduction of the volume of proximal focal zones enables the improved juxtaposing of the sequences of elementary lesions S and S1 when effecting the sectoral trajectories as described in the FIG. 2B. This solution, by reducing the overlapping of focal zones Z in the proximal zone, prevents the overexposure of the proximal zones and intermediate tissues while also provides for the juxtaposition of focal zones Z in the distal zone.

The invention is not limited to the examples described and represented herein given that various modifications may be made thereto without departing from its scope.

The invention claimed is:

1. An apparatus for reducing treatment time during thermal treatment of a treatment zone in biological tissue using an application of focused ultrasound waves, the apparatus comprising:

an ultrasound probe configured to deliver focused ultrasound energy in a focal zone of the treatment zone, wherein the focal zone is located at a distance from the ultrasound probe;

a control system comprising:

a control circuit for controlling the ultrasound probe so as to move the focal zone along a predetermined scan path trajectory, and for controlling an ultrasonic power delivered by the ultrasound probe, in relation to a position of the ultrasound probe, in a form of a repetition of ultrasonic pulses, each being separated by a waiting time and having an emission time whose ratio to a period of repetition of ultrasonic pulses defines a duty cycle, wherein the control system comprises:

a probe movement system configured to move the focal zone along a first direction to juxtapose the treatment zones, and to create a sequence of treatment zones, and along at least one second direction that is different from the first direction, in order to completely cover the treatment zone; the probe movement system ensuring, on the one hand, the moving of the focal zone from a distal point of the treatment zone to a proximal point of the treatment zone in order to create the sequence of treatment zones along the first direction; and, on the other hand, the juxtaposition along the second direction of sequences of treatment zones juxtaposed along the first direction, for each of the sequences of treatment zones, the focal zone being moved from the distal point of the treatment zone to the proximal point of the treatment zone;

wherein the ultrasonic power decreases between a position of the ultrasound probe at the distal point of the treatment zone and a position of the ultrasound probe at the proximal point of the treatment zone, for each of the sequences of treatment zones; and wherein the control system outputs signals in order to ensure the reduction of the ultrasonic power emitted in accordance with a correction law $p_i$, wherein:

$$p_i = P_{ref} \exp(Ad_i);$$

where:

$p_i$ = a power required for a focal zone at a depth $d_i$;

$P_{ref}$ = a reference power;

A = an attenuation coefficient; and wherein the treatment time during the thermal treatment of the treatment zone in the biological tissue is reduced.

2. The apparatus according to claim 1, wherein the control circuit outputs signals for activating the ultrasound probe, to ensure that the duty cycle ratio of the ultrasonic pulses delivered by the ultrasound probe for creating the sequences of treatment zones is between 65% and 100%.

3. The apparatus according to claim 1, wherein the control system moves the focal zone along the acoustic axis that serves as a first direction.

4. The apparatus according to claim 1, wherein the probe movement system is a mechanical system.

5. The apparatus according to claim 1, wherein the ultrasound probe comprises a plurality of ultrasound emitters, and wherein the probe movement system is an electronic system.

6. The apparatus according to claim 5, wherein the control system outputs signals to activate the ultrasound emitters so that an aperture number of the probe decreases when the focal zone passes from the distal point to the proximal point.

7. The apparatus according to claim 1, wherein the control system outputs signals to activate the ultrasound emitters.

8. The apparatus according to claim 1, wherein the duty cycle ratio is between 85% and 100%.

* * * * *